United States Patent [19]

Hillstead

[11] Patent Number: 4,874,378

[45] Date of Patent: Oct. 17, 1989

[54] CATHETER SHEATH INTRODUCER

[75] Inventor: Richard A. Hillstead, Hollywood, Fla.

[73] Assignee: Cordis Corporation, Miami, Fla.

[21] Appl. No.: 201,473

[22] Filed: Jun. 1, 1988

[51] Int. Cl.⁴ .......................................... A61M 25/00
[52] U.S. Cl. ................................... 604/167; 604/283; 604/264
[58] Field of Search .............................. 604/158–170, 604/174–175, 264, 275–279, 272–274, 283

[56] References Cited

U.S. PATENT DOCUMENTS

| 3,017,887 | 1/1962 | Heyer | 604/175 |
| 4,610,674 | 9/1986 | Suzuki et al. | 604/167 X |
| 4,686,977 | 8/1987 | Cosma | 128/DIG. 26 |

Primary Examiner—Dalton L. Truluck
Attorney, Agent, or Firm—Tarolli, Sundheim & Covell

[57] ABSTRACT

The improved catheter sheath introducer serves the purpose of introducing a catheter or the like into a patient's body vessel. The introducer includes a hollow housing having a pasageway extending through the proximal and distal ends of the housing so that an elongated catheter may slide through the housing from the proximal end to the distal end thereof before introduction into a body vessel. A cannula extends from the distal end of the housing and is adapted to be inserted into the body vessel and is in communication with the passageway of the housing. Thus, the catheter may slide through the distal end of the housing and then through the cannula into the body vessel. A flexible coupling connects one end of the cannula with the housing distal end in such a manner that the cannula may be angularly displaced with respect to the distal end of the housing without bending the cannula itself.

10 Claims, 2 Drawing Sheets

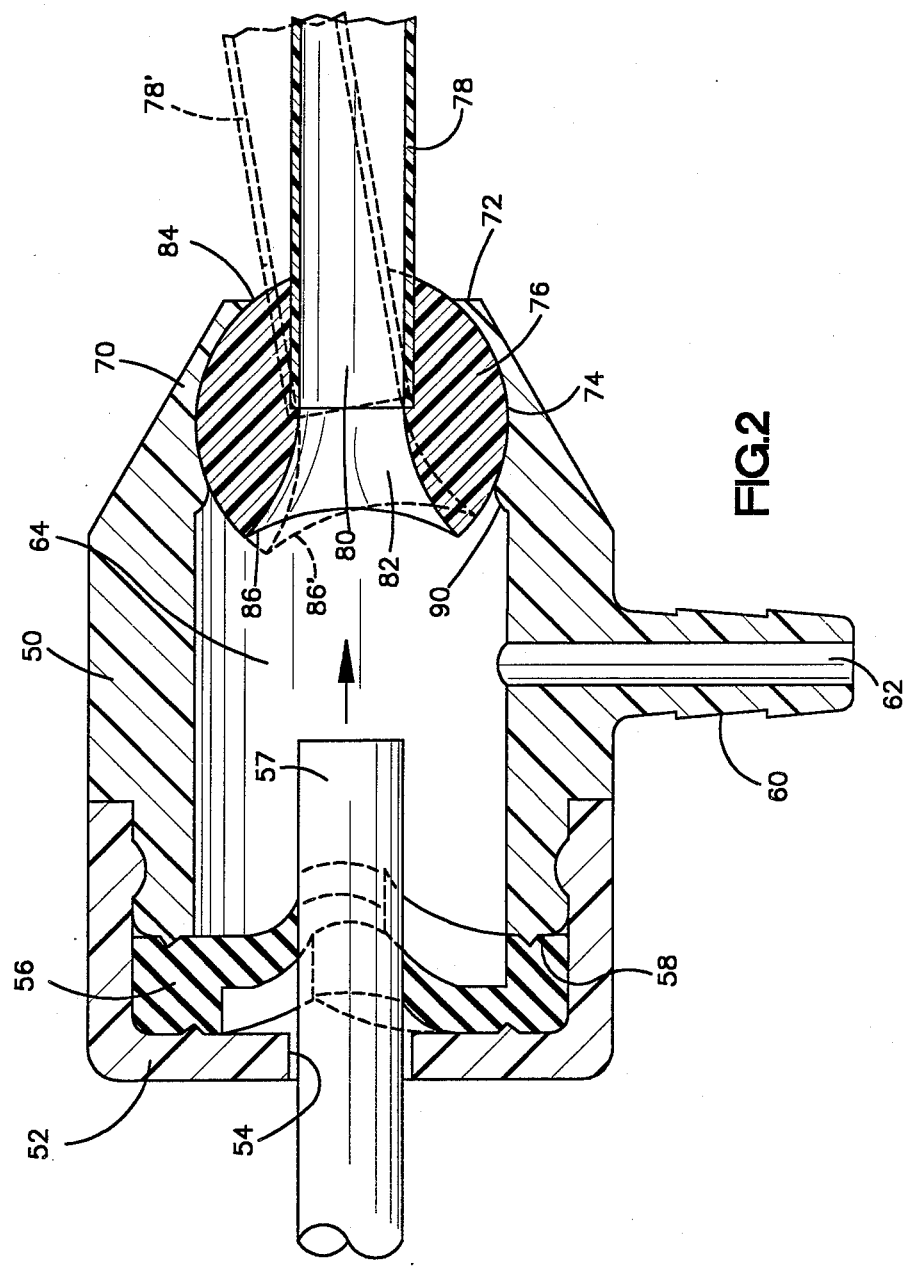

CATHETER SHEATH INTRODUCER

BACKGROUND OF THE INVENTION

This invention relates to the art of catheter sheath introducers and, more particularly, to improvements permitting rotational and angular movement of a cannula relative to the distal end of the housing of such an introducer.

Catheter sheath introducers are known in the art and examples are described in the patents to L. A. Weinstein U.S. Pat. No. 4,626,245 and R. C. Stevens U.S. Pat. No. 4,000,739. These catheter sheath introducers typically take the form of a molded plastic tubular housing having a distal end and a proximal end and having a passageway extending through the proximal and distal ends and the housing for slideably receiving an elongated catheter tube. The catheter tube may slide through the housing from the proximal end to the distal end before being introduced into a body vessel. A tubular cannula extends from the distal end of the housing and is adapted to be inserted into a body vessel and be in communication with the passageway through the housing. The cannula serves to guide a catheter passing through the housing and thence through the cannula and into the body vessel. Typically, the catheter sheath introducer is secured to the exterior of a body, such as on an arm, with the cannula in place within a body vessel, such as an artery. The catheter may then be slid through the introducer and be guided by the cannula into the body vessel. As is typically accomplished during angiographic procedures, the catheter serves to insert x-ray contrast fluid into a body vessel, such as an artery.

The cannula is a plastic tube which fits within the housing as by a press fit or the like, and extends therefrom so as to be inserted into the body vessel. The physician will insert the cannula tube sufficiently far into a body vessel that the distal end of the housing bears up against a patient's body, the arm, for example. The introducer is then held in place by taping it to the patient's arm. One problem that has been encountered with this procedure is that there is a tendency for the cannula to be angularly displaced relative to the distal end of the housing, causing the cannula to take on a bend or become kinked. This kinking takes place at the junction of the cannula and the distal end of the housing and causes a reduction in the inner diameter at the junction. This provides an obstruction as the physician is trying to slide a catheter through the introducer and into the cannula. Because of the small diameters employed with catheters in this procedure, any reduction in the inner diameter of the cannula tube presents difficulties for the physician in attempting to insert catheter through the introducer and thence through the cannula into a patient's body vessel.

SUMMARY OF THE INVENTION

It is, therefore, an object of the present invention to provide an improved catheter sheath introducer which minimizes the reduction in diameter at the junction of the distal end of the housing and the cannula tube when the tube is angularly displaced relative to the housing, as in the case described hereinabove.

In accordance with the present invention, the improved catheter sheath introducer includes a hollow housing having proximal and distal ends. A passageway extends through the proximal and distal ends and the housing, so as to thereby slideably receive an elongated catheter tube such that the catheter tube may pass through the housing from the proximal end to the distal end thereof, before introduction into a body vessel. A tubular cannula extends from the distal end of the housing and is adapted to be inserted into the body vessel. This cannula is in communication with the passageway within the housing so the catheter may slideably extend through the distal end of the housing and thence through the cannula and into the body vessel. A flexible coupling interconnects a first end of the cannula with the distal end of the housing in such a manner that the cannula may be angularly displaced with respect to the housing without bending the cannula itself.

In accordance with a still further aspect of the present invention, the flexible coupling takes the form of a ball and socket arrangement, including a ball member and a socket member with one of the members being carried by the housing, and the other of the members being carried by a first end of the cannula.

In accordance with a still further aspect of the present invention, the ball member is carried by the first end of the cannula and the socket member is carried by the distal end of the housing. The ball member has a passageway extending therethrough in communication with the cannula so that a catheter may be slideably received through the passageways, including that within the ball member, and thence through the cannula before introduction into a body vessel.

In accordance with a still further aspect of the present invention, the ball and socket arrangement permits the introducer housing to be rotated about an axis containing the passageway whereby a physician may make adjustments to the positioning of the introducer without impairing the application thereof.

DESCRIPTION OF THE DRAWINGS

The foregoing and other objects of the invention will become more readily apparent from the following description of the preferred embodiment of the invention, as taken in conjunction with the accompanying drawings which are a part hereof and wherein:

FIG. 2 is an exploded, partially cut-away view of a preferred embodiment of the present invention.

DESCRIPTION OF THE PREFERRED EMBODIMENT

Figure 1:
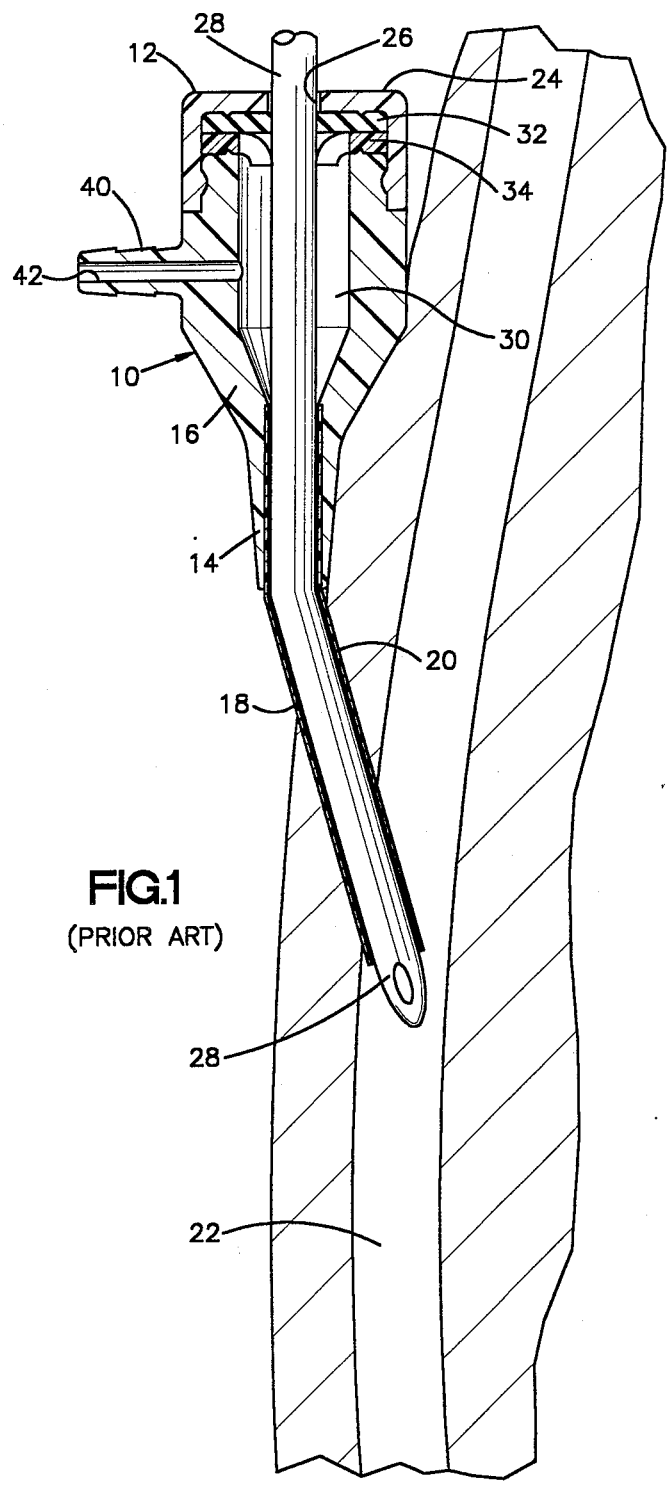
FIG. 1 is a view partially in cross section, showing a catheter sheath introducer of the prior art in position with the cannula inserted within a blood vessel.

Reference is now made to the drawings, wherein FIG. 1 represents a catheter sheath introducer of the prior art such as that illustrated in the patent to R. C. Stevens, U.S. Pat. No. 4,000,739. As illustrated, the introducer is constructed of a molded plastic housing 10 having a proximal end 12 and a distal end 14. At the distal end, there is a tubular protrusion 16 which has a cylindrical-shaped inner wall which carried a cannula 18 which has an outer diameter corresponding with the inner diameter of the protrusion 16. The parts may be held in place as with a pressfit or a suitable bonding agent may be employed. The cannula is an elongated tube which extends from the distal end 14 of the housing and is intended to protrude through an opening 20 in a patient's body, such as an arm, so that the distal end of the cannula may be received within a body vessel, such as an artery 22 of the patient.

The housing 10 has an end cap 24 mounted on its distal end and the end cap has a hole 26 formed therein of sufficient diameter to permit a catheter 28 to be extended through the hole and thence through interior passageway 30 within the housing and thence through the cannula 18 which guides the movement of the distal end of the catheter for introduction into the patient's blood vessel or artery 22. The housing also carries an annular gasket 32 having a centrally located hole in alignment with end cap hole 26 and being of a diameter sufficient for slideably receiving catheter 28. The housing also carries a hemostatis valve 34. Gasket 32 and valve 34 are held in place at the distal end of the housing by means of the end cap 24 when properly positioned on the distal end of the housing. The hemostatis valve 34 and the annular gasket 34 may take the form as illustrated in the patent to R. C. Stevens U.S. Pat. No. 4,000,739. It may be constructed of latex, silicon rubber, or other suitable sealing material. The valve 34, for example, may have a Y-slit located therein, so that the valve may be penetrated by catheter 28 in such a manner to prevent backflow of blood through the valve when the catheter is in place, as shown in FIG. 1, or when entering into or exiting from the housing and when the catheter is not being employed at all. Alternatively, the gasket 32 and valve 34 may be replaced by a single hemostatis valve, such as that illustrated in the patent to L. A. Weinstein U.S. Pat. No. 4,626,245.

As shown in FIG. 1, a boss 40 extends radially from the housing and contains a passageway 42 which is in commuication with the interior passageway 30 of the housing. The boss 40 is stepped on its exterior to provide means for connection with a plastic tube by which a liquid may be introduced through passageway 42 into the housing for purposes of flushing the interior of the housing and also by which a physician may introduce a saline solution under a positive pressure during the operation.

With the introducer in place, as shown in FIG. 1, the physician will tape the introducer to the patient's body. It will be noted from FIG. 1 that the cannula 18 is bent at an angle to the housing at a point where the cannula exits from the housing. Depending on the severity of this bend, a kinking will take place causing the interior diameter of the cannula to decrease. If a physician now inserts a catheter into the housing, he will note an obstruction as the distal end of the catheter tries to pass through the bent cannula. Depending on the extent of the bend, the physician may not be able to successfully slide the distal end of the catheter past that location. A physician typically rotates a catheter about its longitudinal axis while manipulating the catheter within the patient. Such a bend or kink at the distal end 14 of the housing will provide a continuous annoyance. This may cause a loss of feel which is important to the physician while manipulating the catheter.

The present invention is directed to an improved catheter sheath introducer similar to that as shown in FIG. 1, but employing a flexible coupling for interconnecting the distal end of the introducer housing with the cannula. With this construction, as will be seen with reference to FIG. 2, the cannula may be angularly displaced relative to the housing by a substantial angle while preventing any kinking and the like, as in the case of the prior art of FIG. 1. Moreover, with this construction, the physician may rotate the introducer housing about its axis in order to reposition the housing relative to the patient without disturbing the positioning of the cannula within the patient's artery or the like. This improved construction is illustrated in FIG. 2, to which attention is now directed.

As shown in FIG. 2, the improved catheter sheath introducer includes an elongated housing 50 which may be constructed from molded plastic. As in the case of the prior art shown in FIG. 1, the housing 50 is fitted with an end cap 52 having a hole 54 centrally located therein so that a catheter 57 may be inserted therethrough and thence through a penetratable hemostatis valve 56 which is held in place on the proximal end 58 of the housing 50 by means of an end cap 52. The hemostatis valve 56 may take the form as shown in FIG. 1 or may be a one-piece valve as illustrated in FIG. 2. Such a one-piece valve, for example, is shown in the patent to L. A. Weinstein U.S. Pat. No. 4,626,245. The valve is comprised of an elastomeric partition having slits cut into its opposite faces so that a catheter or the like may penetrate therethrough while preventing blood or the like from leaking through the valve. Also, as in the case of the prior art in FIG. 1, the housing 50 is provided with a radially extending boss 60 having a passageway 62 extending therethrough and which communicates with the passageway 64 within the housing 50 so that saline fluid and the like may be supplied into the housing.

The housing 50 is a cylindrical body having a tapered protrusion 70 extending from the cylindrical body toward the distal end 72 of the housing. The inner walls or the protrusion 70 are formed so as to define a socket 74 having a curvature corresponding with that of a ball 76 secured to one end of a cannula 78. The ball 76 may be constructed of plastic and the cannula 78 extending therefrom may be a separate part which has been secured to the ball or the ball and cannula may be constructed from molded plastic as an integral unit. As shown, the ball 76 has a cylindrical passageway 80 which extends into the ball to approximately the midpoint thereof and then flares outwardly in a conical manner so as to provide a flared or funnel-like wall 82. A portion of the length of the cannula may be inserted within the cylindrical opening 80 and held in place, as with a pressfit or by a suitable bonding material. The distal end 72 of the housing has a circular opening 84 which is substantially smaller in diameter than that of ball 76 and is of substantially the same diameter as the funnel opening 86. This permits the ball 76 to rotate about its center within the limits of travel of cannula 74 which engages the opening 84 at the distal end 72 of the housing. This is indicated in dotted lines in FIG. 2 with the character identification 78'. While the cannula is so angularly displaced, the funnel opening 86 will be positioned as shown in dotted lines with the character 86'. This will permit entrance of the distal end of catheter 57 so that the catheter may be guided through the ball by the funnel walls 82, and thence into the cannula which will then guide the catheter into a patient's body cavity, such as the artery 22 of FIG. 1.

The protrusion 70 of housing 50 is constructed of plastic material and, hence, exhibits a degree of resiliency so that, in some applicaations, the ball may be inserted into the socket 74 by way of the opening 84, although some modification in the opening size would be required to achieve this. Preferably, however, the ball, with the cannula attached thereto, is inserted into the housing through the proximal end thereof until it rests within the socket 74. The ball is held in place by means of a ball retainer ring 90 which is formed within the inner walls of the housing, and extends coaxially about the housing's axis. This ball retainer ring is sufficiently resilient that the ball may be inserted into the socket while also preventing the ball from being displaced toward the proximal end of the housing during normal operation.

The ball 76 is preferably constructed of molded plastic. Typically, such a catheter sheath introducer is considered a disposable item and is disposed of after one application to a patient. Conceivably, situations may arise that the introducer would be sterilized for subsequent use. In which case, it may be desirable to construct the ball 76 of metal, such as stainless steel.

Whereas the retainer ring 90 has been illustrated as being a molded part within the housing, it could also take the form of a separate O-ring or a gasket which would be mounted in the interior walls of the housing and positioned so as to hold the ball 76 in place in the socket 74.

In the application of the improved catheter sheath introducer of FIG. 2, the introducer would be applied in the manner as discussed hereinbefore with respect to FIG. 1. Thus, with the catheter removed, the introducer will be positioned adjacent the patient's body and the cannula will be inserted into a patient's blood vessel such as the artery of FIG. 1. The cannula will be inserted sufficiently far that the distal end 72 of the introducer bears against the patient's skin and the cannula may be displaced at an angle relative to the distal end of the housing such as at the position 78' shown in FIG. 2, without bending or placing a kink in the cannula. The physician may now rotate housing 50 to properly position the boss 60 to satisfy the physician and then tape the introducer in place against the patient's body. Therefter, the physician may insert the catheter 57 through the end cap hole 54 and thence through the hemostasis valve 56 so that the distal end of the catheter will be received by the conical funnel walls 82 and be guided into the cannula 78 through which the catheter may be futher displaced so that the distal end thereof extends beyond the distal end of the cannula and into the patient's blood vessel, such as the artery 22 of FIG. 1.

Various modifications may be made to that as shown in the drawings herein without departing from the scope and spirit of the invention as defined by the appended claims.

I claim:

1. A catheter sheath introducer for use in introducing a catheter into the body vessel and comprising:
   a tubular housing having proximal and distal ends and having a passageway extending through said proximal and distal ends and the housing for slideably receiving an elongated catheter so that the catheter may pass through the housing from said proximal end to said distal end before introduction into a said body vessel;
   a tubular cannula extending from the distal end of said housing but not directly connected to said housing and adapted to be inserted into a said body vessel and being in communication with said passageway so that said catheter may slideably extend through the distal end of said housing and thence through said cannula and into a said body vessel;
   flexible coupling means connecting a first end of said cannula with said housing at the distal end thereof without any significant overlap between said first end and said housing and in such a manner that said cannula may be angularly displaced with respect to the distal end of said housing, without any bending of said cannula so that said cannula does not deform.

2. A catheter sheath introducer as set forth in claim 1 wherein said flexible coupling means includes a ball and socket arrangement including a ball member and a socket member with one of said members being carried by said housing and the other of said members being carried by a first end of said cannula.

3. A catheter sheath introducer as set forth in claim 2 wherein said ball member has a passageway extending therethrough and which is in communication with that of said housing and of said cannula so that a said catheter may be slideably received and passed therethrough before introduction into a said body vessel.

4. A catheter introducer as set forth in claim 3 wherein said ball member is caried by said first end of said cannula and said socket member is carried by said housing.

5. A catheter sheath introducer as set forth in claim 4 wherein said housing has inwardly facing walls which are curved to define said socket member having a curvature corresponding with that of said ball member for receiving said ball member in such a manner that said ball member may rotate within said socket member without being dislodged from said housing.

6. A catheter sheath introducer as set forth in claim 5 including ball retaining means located within said housing intermediate said socket member and the proximal end of said housing for retaining said ball member in place within said socket member.

7. Apparatus as set forth in claim 6 wherein said ball retaining means is an annular ring extending radially inward from the inner walls of said housing and integral therewith.

8. Apparatus as set forth in claim 5 wherein said passageway extending through said ball member flares outwardly in a conical fashion to form a funnel-like opening facing the proximal end of said housing for receiving and guiding the distal end of a said catheter as it is being passed through said ball member into said cannula.

9. Apparatus as set forth in claim 8 wherein the distal end of said housing has a circular opening of a diameter substantially greater than that of said cannula permitting said ball member to rotate within said socket member while permitting angular displacement of said cannula relative to the distal end of said housing without bending said cannula itself.

10. A catheter sheath introducer as set forth in claim 9 wherein said opening in said distal end of said housing is of a diameter corresponding essentially with that of said funnel opening in said ball member.

* * * * *